United States Patent
Omote et al.

(10) Patent No.: US 9,250,199 B2
(45) Date of Patent: Feb. 2, 2016

(54) X-RAY IMAGING APPARATUS, AND X-RAY IMAGING METHOD

(71) Applicant: Rigaku Corporation, Tokyo (JP)

(72) Inventors: Kazuhiko Omote, Akiruno (JP); Yoshihiko Takeda, Ome (JP)

(73) Assignee: RIGAKU CORPORATION (JP)

( * ) Notice: Subject to any disclaimer, the term of this patent is extended or adjusted under 35 U.S.C. 154(b) by 0 days.

(21) Appl. No.: 13/925,144

(22) Filed: Jun. 24, 2013

(65) Prior Publication Data

US 2014/0003578 A1     Jan. 2, 2014

(30) Foreign Application Priority Data

Jun. 29, 2012   (JP) .................................. 2012-147719

(51) Int. Cl.
| | |
|---|---|
| *G01N 23/04* | (2006.01) |
| *A61B 6/00* | (2006.01) |
| *A61B 8/08* | (2006.01) |

(52) U.S. Cl.
CPC ............... *G01N 23/04* (2013.01); *A61B 6/5235* (2013.01); *A61B 6/5241* (2013.01); *A61B 8/5253* (2013.01)

(58) Field of Classification Search
CPC ....... G01N 23/00; G01N 23/04; G01N 23/06; A61B 60/02; A61B 6/04; A61B 6/0457; A61B 6/504; A61B 6/587; A61B 6/588; A61B 6/4405; A61B 6/4429; A61B 6/5235; A61B 6/5241; A61B 8/5253
USPC ........ 378/51, 62, 63, 91, 98.8, 102, 114, 115, 378/116, 164, 165, 175, 181, 197, 208, 209
See application file for complete search history.

(56) References Cited

U.S. PATENT DOCUMENTS 5,032,990 A * 7/1991 Eberhard et al. ................... 378/4
5,319,693 A * 6/1994 Eberhard et al. ................ 378/19
(Continued)

FOREIGN PATENT DOCUMENTS

| DE | 4016245 A1 | 12/1990 |
|---|---|---|
| DE | 102005062582 A1 | 7/2007 |

(Continued)

OTHER PUBLICATIONS

Rau et. al., Imaging of micro- and nano-structures with hard X-rays, Mar. 2007, Micro & Nano Letters, vol. 2, No. 1, p. 1-3.*
(Continued)

*Primary Examiner* — David J Makiya
*Assistant Examiner* — Julio M Duarte-Carvajalino
(74) *Attorney, Agent, or Firm* — Cantor Colburn LLP (57) ABSTRACT

An X-ray imaging apparatus and an X-ray imaging method that can stitch transmission images detected by a two-dimensional detector at different positions of the sample are provided. An X-ray imaging apparatus and an X-ray imaging method include: an X-ray generating unit configured to irradiate a sample with a substantially parallel X-ray; a two-dimensional detector including a detection region; a stage where a support base is mounted is configured to move the support base in a plane along a plane of the detection region; and an imaging control unit configured to generate stitched transmission image data based on a plurality of transmission images of the sample detected by the two-dimensional detector. The imaging control unit is configured to stitch the transmission images at a plurality of mutually different positions in the sample to generate the stitched transmission image data.

9 Claims, 10 Drawing Sheets

(56) References Cited

U.S. PATENT DOCUMENTS

| | | | |
|---|---|---|---|
| 6,447,163 B1* | 9/2002 | Bani-Hashemi et al. | 378/205 |
| 7,545,905 B2 | 6/2009 | Munker et al. | |
| 2003/0215060 A1* | 11/2003 | Ohzawa | 378/154 |
| 2007/0280421 A1* | 12/2007 | Cho et al. | 378/158 |
| 2009/0141958 A1 | 6/2009 | Graumann et al. | |
| 2009/0290680 A1* | 11/2009 | Tumer et al. | 378/62 |
| 2012/0087470 A1 | 4/2012 | Omote et al. | |

FOREIGN PATENT DOCUMENTS

| | | |
|---|---|---|
| JP | S63157046 A | 6/1988 |
| JP | 07209213 A | 8/1995 |
| JP | 9-101270 A | 4/1997 |
| JP | H11295242 A | 10/1999 |
| JP | 2004012200 A | 1/2004 |
| JP | 2006317249 A | 11/2006 |
| JP | 2006322799 A | 11/2006 |
| JP | 2008032754 A | 2/2008 |
| JP | 2009139314 A | 6/2009 |
| JP | 2011169711 A | 9/2011 |
| JP | 2012-80963 A | 4/2012 |

OTHER PUBLICATIONS

Japanese Office Action corresponding to Application No. 2012-147719; Dated: Aug. 11, 2015.

* cited by examiner

FIG.8 j-TH OVERLAPPING AMOUNT Δj i-TH    i+1-TH

X-RAY IMAGING APPARATUS, AND X-RAY IMAGING METHOD

CROSS-REFERENCE TO RELATED APPLICATION

The present application claims priority from Japanese application JP 2012-147719, filed on Jun. 29, 2012, the content of which is hereby incorporated by reference into this application.

BACKGROUND OF THE INVENTION

1. Field of the Invention

The present invention relates to an X-ray imaging apparatus and an X-ray imaging method. Especially, this invention relates to the X-ray imaging where a transmission image of a sample is larger than a detection region (screen) of a two-dimensional detector.

2. Description of the Related Art

In the field of X-ray transmission imaging, a two-dimensional detector is used. The detection region and resolution of the two-dimensional detector are limited. Conventionally, in order to obtain a high-resolution transmission image, a microfocus X-ray source has been used, and a sample has been brought close to the X-ray source, thus obtaining an enlargedly projected transmission image of the sample. That is, reducing the distance from the X-ray source to the sample and sufficiently taking the distance from the sample to the detector can achieve a high-resolution. Then, by adjusting the distance relationship, it is possible to adjust the magnification. JP 09-101270 A discloses a technique that detects an enlarged image that is generated by transmission of an X-ray with large divergence angle through a sample.

SUMMARY OF THE INVENTION

Although a high-resolution transmission image can be obtained by bringing a sample close to an X-ray source, this makes a measurable region (single shot region) of the sample, which is detectable by a two-dimensional detector with single capture of the transmission image, smaller than can be. When the sample is larger than the measurable region of the sample, a part of the sample is merely taken in the obtained X-ray image. That is, it is difficult to achieve both resolution improvement of the taken transmission image and enlargement of the measurable region at the same time.

In order to obtain a wider range of the X-ray image while improving the resolution of the image, the inventors examined an X-ray imaging apparatus with a two-dimensional XY stage. This is assumed to be an X-ray imaging apparatus according to Comparative example 1. A sample is mounted on the two-dimensional XY stage, and the sample can be moved along a plane (xy plane) parallel to the plane of the detection region of the two-dimensional detector. If the sample is moved sequentially by the two-dimensional XY stage, and the transmission images are taken sequentially to stitch a plurality of transmission images to generate stitched transmission image data, this may achieve a generation of a high-resolution X-ray image with a wider range (for example, the whole sample). However, the sample has a finite thickness along a direction (z direction) perpendicular to the detection region of the two-dimensional detector, thus the following problems occur.

Figure 9A:
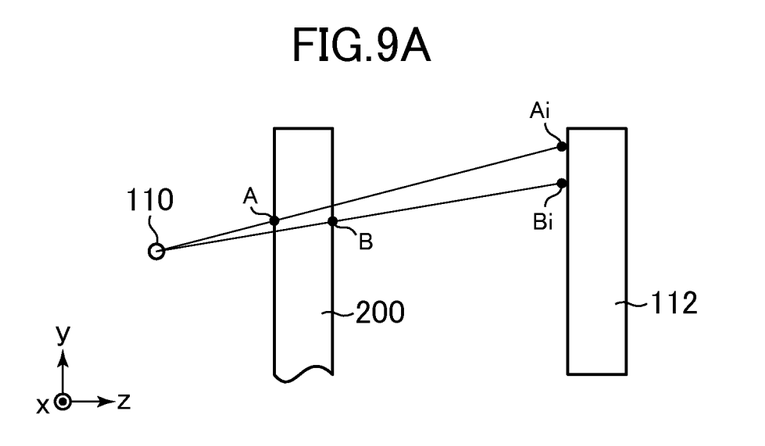
FIGS. 9A and 9B are schematic views illustrating an operation of the X-ray imaging apparatus according to Comparative example 1.
Figure 9B:
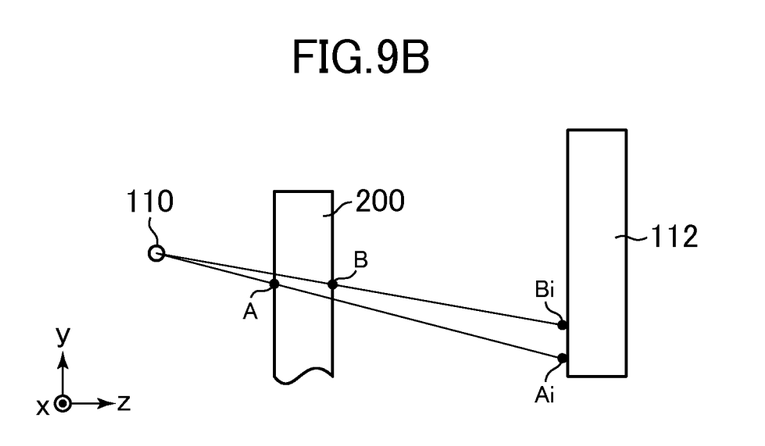

FIGS. 9A and 9B are schematic views illustrating an operation of the X-ray imaging apparatus according to Comparative example 1. In the X-ray image where an enlarged projection is performed by an X-ray emitted from an X-ray source 110, a two-dimensional detector 112 detects two points, which are located at the same position in the xy plane of a sample 200 and are located at the different positions in the z direction, at different positions. Assuming that the sample has a plane plate shape, and a point A is on a surface at an X-ray source side and a point B is on a surface at a two-dimensional detector side and these points are located in the same position in the xy plane. In FIG. 9A, since these two points are located in an upper side of the drawing with respect to the X-ray source 110, the X-ray passing through the point A at the X-ray source 110 side diverges to the upper side as compared with the X-ray passing through the point B at the two-dimensional detector 112 side. An image Ai of the point A is located in the upper side of the drawing as compared to an image Bi of the point B in the X-ray image obtained by the two-dimensional detector 112. In contrast to this, in FIG. 9B, since these two points are located in the lower side of the drawing with respect to the X-ray source 110, the X-ray passing through the point A diverges further to the lower side as compared with the X-ray passing through the point B, and the image Ai of the point A is located in the lower side of the drawing as compared with the image Bi of the point B. Therefore, in an attempt to stitch these two transmission images, for example, even if the images are stitched in the position of the image Ai of the point A, the position shift of the image Bi of the point B occurs, thus the X-ray imaging apparatus according to the Comparative example 1 cannot achieve a wide range with a high-resolution X-ray image.

The present invention has been made to solve the above-described problems, and it is an object of the present invention to provide an X-ray imaging apparatus and an x-ray imaging method that can stitch transmission images detected by a two-dimensional detector a sample at different positions with respect to the two-dimensional detector.

(1) To solve the above-described problems, an X-ray imaging apparatus according to the present invention includes: an X-ray generating unit, a two-dimensional detector, a support base, a stage, and a control unit. The X-ray generating unit is configured to irradiate a sample with a substantially parallel X-ray. The two-dimensional detector is arranged at an opposite side of the X-ray generating unit with respect to the sample. The two-dimensional detector includes a detection region to detect a transmission image of the sample. The sample is arranged on the support base. The stage where the support base is mounted is configured to move the support base in a plane along a plane of the detection region of the two-dimensional detector. The control unit is configured to generate stitched transmission image data based on a plurality of transmission images of the sample detected by the two-dimensional detector. The control unit is configured to stitch the transmission images at a plurality of mutually different positions in the sample to generate the stitched transmission image data.

(2) An X-ray imaging apparatus described in (1) above may have the following configuration. The support base includes a rotational drive system with a rotation axis in a direction along the plane of the detection region. The rotational drive system is configured to rotationally move the sample to a predetermined number of respective angular positions. The control unit is configured to: stitch the transmission images at the plurality of mutually different positions in the sample in the predetermined number of respective angular positions to generate the stitched transmission image data; and perform image reconstruction with the predetermined number of pieces of stitched transmission image data generated so as to obtain a three-dimensional X-ray CT image.

(3) An X-ray imaging apparatus described in (2) above may have the following configuration. The stage is configured to sequentially move the support base to arrange the sample in a position among the plurality of mutually different positions. In the arrangement of the position, the rotational drive system rotationally moves the sample to sequentially arrange the sample in an angular position among the predetermined number of angular positions. In the arrangement, the two-dimensional detector detects a transmission image of the sample. In the predetermined number of respective angular positions, a plurality of transmission images are detected in the plurality of mutually different positions in the sample.

(4) The X-ray imaging apparatus described in any of (1) to (3) above may have the following configuration. The optical capture unit is configured to capture an optical image of the sample. The optical mirror is arranged between the X-ray generating unit and the support base. The optical mirror is configured to allow an X-ray to pass from the X-ray generating unit to the sample. The optical mirror is configured to reflect light travelling from the sample along a normal direction to the plane of the detection region to enter the light into the optical capture unit.

(5) An X-ray imaging apparatus described in (4) above may have the following configuration. The optical mirror includes an opening portion through which an X-ray passes. The X-ray reaches the detection region of the two-dimensional detector from the X-ray generating unit.

(6) The X-ray imaging apparatus described in (4) above may have the following configuration. The optical mirror is a metal thin film mirror.

(7) The X-ray imaging apparatus described in any of (1) to (6) above may have the following configuration. Assuming that a distance from the X-ray generating unit to the sample is L and a distance from the sample to the two-dimensional detector is d, a value of d/L is equal to or less than 0.1.

(8) The X-ray imaging apparatus described in any of (1) to (7) above may have the following configuration. Regarding an X-ray that enters the sample and passes through the sample to reach the detection region of the two-dimensional detector, assuming that a distance from an incident position to an outgoing position in the sample is t and an angle between a normal direction to the detection region and a traveling direction of the X-ray is θ, t is sufficiently larger than a spatial resolution of the two-dimensional detector and tθ is extent of equal to or less than the spatial resolution of the two-dimensional detector.

(9) An X-ray imaging method according to the present invention uses an X-ray generating unit, a two-dimensional detector, a support base, a stage, and a control unit. The X-ray generating unit is configured to irradiate a sample with a substantially parallel X-ray. The two-dimensional detector is arranged at an opposite side of the X-ray generating unit with respect to the sample. The two-dimensional detector includes a detection region to detect a transmission image of the sample. The sample is arranged on the support base. The stage where the support base is mounted is configured to move the support base in a plane along a plane of the detection region of the two-dimensional detector. The control unit is configured to generate stitched transmission image data based on a plurality of transmission images of the sample detected by the two-dimensional detector. The control unit is configured to stitch the transmission images at a plurality of mutually different positions in the sample to generate the stitched transmission image data.

The present invention provides an X-ray imaging apparatus and an X-ray imaging method that can stitch transmission images in which a two-dimensional detector detects a sample at different positions with respect to the two-dimensional detector.

DETAILED DESCRIPTION OF THE INVENTION

Embodiments of the present invention will be specifically described in detail in the following by referring to the accompanying drawings. Note that the drawings referred to in the following are only for illustrating the embodiments by way of examples, and are not necessarily drawn to scale. Further, in the following drawings, like reference numerals designate members having the same functions, and the repeated description are omitted except as required.

First Embodiment

Figure 1:
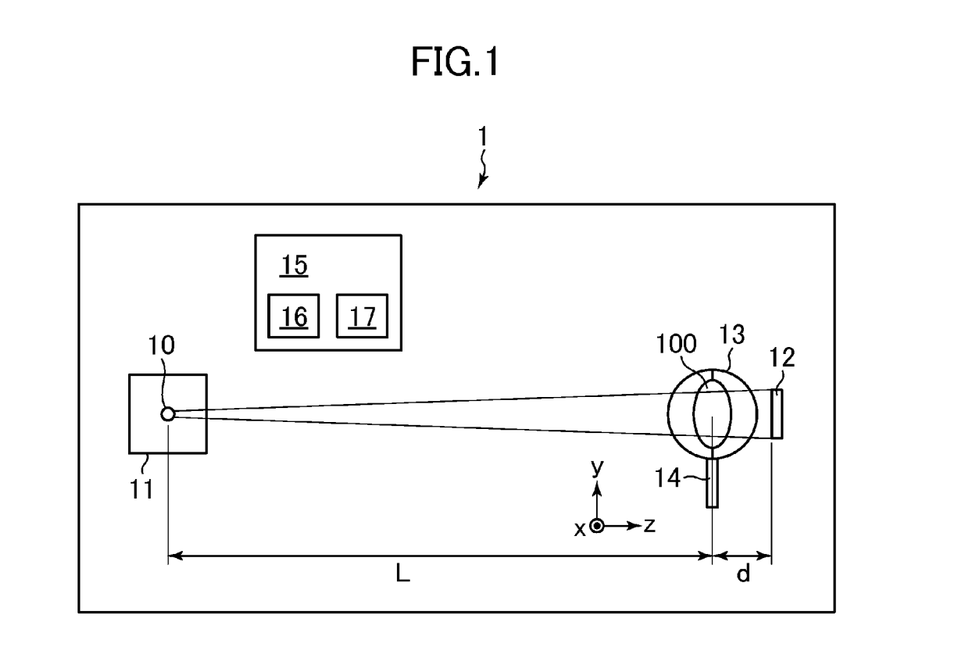
FIG. 1 is a schematic view illustrating a structure of an X-ray imaging apparatus according to a first embodiment of the present invention.

FIG. 1 is a schematic view illustrating a structure of an X-ray imaging apparatus 1 according to a first embodiment of the present invention. The X-ray imaging apparatus 1 according to the embodiment is an X-ray imaging apparatus of a two-dimensional X-ray transmission image. The X-ray imaging apparatus 1 includes an X-ray generating unit 11 having an X-ray source 10, a two-dimensional detector 12, a support base 13 supporting a sample 100, a two-dimensional XY stage 14 where the support base 13 is mounted, and a control unit 15.

The main features of the X-ray imaging apparatus 1 according to the embodiment are that divergence of the X-ray emitted from the X-ray generating unit 11 to the sample 100 is reduced and a substantially parallel X-ray beam is made, and that the X-ray imaging apparatus 1 includes a stage which can move the sample 100 along a plane of a detection region of the two-dimensional detector 12. This allows the X-ray imaging apparatus 1 to stitch transmission images of the sample 100 at a plurality of different positions with respect to the two-dimensional detector 12, thus generating a stitched transmission image data (large FOV (Field of View) transmission image). A significant effect is achieved in the case where transmission image of the whole sample 100 is greater than the detection region of the two-dimensional detector 12 by the X-ray imaging apparatus according to the present invention.

The configuration of the X-ray imaging apparatus 1 according to the embodiment will be described below.

The X-ray source 10, which is included in the X-ray generating unit 11, is an X-ray source with a finite focus size used in laboratories. The X-ray source 10 uses a metal such as copper (Cu), molybdenum (Mo), tungsten (W), or the like, as a target. In addition, the X-ray source 10 may use a radiation light by synchrotron radiation, which is an ideal collimated X-ray beam source.

The two-dimensional detector 12, for example, is a charge coupled device (CCD), and has a detection region (screen) formed in a planar shape (detection plane/X-ray receiving plane). The two-dimensional detector 12 is not limited to the CCD, and it may be possible to use any X-ray detector that can detect the transmission image of the sample 100. The two-dimensional detector 12 has a high spatial resolution of equal to or less than 10 μm. However, the spatial resolution of equal to or less than 7 μm is preferable, and the spatial resolution of equal to or less than 1 μm is further more preferable. The two-dimensional detector 12 is arranged at an opposite side of the X-ray generating unit 11 with respect to the sample 100. Assume that a plane of the detection region of the two-dimensional detector 12 is an xy plane, and a normal direction (direction perpendicular) to the plane of the detection region is a z direction. It is preferable to arrange the two-dimensional detector 12 such that a straight line extending in the normal direction (the z direction) from a center of the detection region of the two-dimensional detector 12 passes through the sample 100 and reaches the X-ray source 10.

The sample 100 is arranged on the support base 13. The two-dimensional XY stage 14 includes the support base 13 and can move the support base 13 within the xy plane. That is, the two-dimensional XY stage 14 can arrange the sample 100 in a plurality of different positions with respect to the two-dimensional detector 12.

The control unit 15 includes a measurement control unit 16 and an imaging control unit 17. The measurement control unit 16 controls the X-ray generating unit 11, the two-dimensional detector 12, the two-dimensional XY stage 14, and similar so as to obtain information for the transmission images of the sample. The imaging control unit 17 generates stitched transmission image data based on the transmission images of the sample 100 in a plurality of different positions detected by the two-dimensional detector 12.

The X-ray generating unit 11 emits an X-ray that is substantially parallel to the sample 100. In this specification, the X-ray that is substantially parallel is defined by the following. As shown in FIG. 1, the sample 100 is arranged in the vicinity of two-dimensional detector 12, instead of the X-ray generating unit 11. Among straight lines, assume that a straight line extends in the normal direction (z direction) to the plane of the detection region of the two-dimensional detector 12, passes through the sample 100, and reaches the X-ray source 10. Out of the straight line, assume that a length of a line segment from the X-ray source 10 of the X-ray generating unit 11 to the center of the sample 100 is set to a distance L between the X-ray generating unit 11 and the sample 100. Also, assume that a length of a line segment from the center of the sample 100 to the detection region of the two-dimensional detector 12 is set to a distance d between the sample 100 and the two-dimensional detector 12. When the d/L is sufficiently small compared with 1, the X-ray irradiated to the sample 100 can be substantially parallel. Here, the d/L that is sufficiently small compared with 1 means that the d/L is equal to or less than 0.1 and is preferably equal to or less than 0.05. In addition, the technique of irradiating with an X-ray that is substantially parallel to a sample is disclosed in JP 2012-80963 A.

As the X-ray irradiated to the sample 100 is substantially parallel, the position shift caused by the difference of the position in the z direction of the sample 100 can be reduced in the transmission image detected by the two-dimensional detector 12. Note that the position shift means, for example, a position shift (images Ai and Bi) in the transmission image, which is detected by the two-dimensional detector 112, caused by the difference of the position in the z direction (points A and B) shown in FIGS. 9A and 9B. Therefore, even in the case where the sample 100 has a large enough thickness t compared with the spatial resolution $\Delta$ of the two-dimensional detector 12, stitched transmission image data can be generated based on the plurality of transmission images if the divergence of the X-ray is reduced such that the position shift caused by the difference of the position in the z direction of the sample 100 does not occur in the transmission image detected by the two-dimensional detector 12. Here, the thickness t is sufficiently large compared with the spatial resolution $\Delta$ means that the thickness t is equal to or more than 10 times the spatial resolution $\Delta$. The X-ray imaging apparatus 1 according to this embodiment irradiates the sample 100 with X-rays in a substantially parallel, thus ensuring the X-ray imaging of the thick sample 100 with a thickness of equal to or more than 100 times the spatial resolution $\Delta$.

Figure 2:
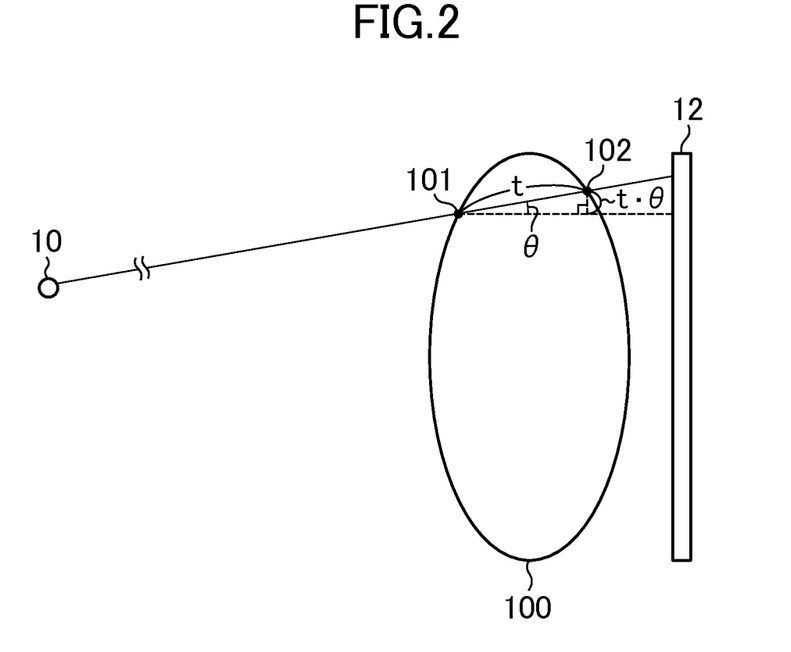
FIG. 2 is a schematic view that describes an X-ray generated by an X-ray generating unit according to the first embodiment of the present invention.

FIG. 2 is a schematic view that describes the X-ray generated from the X-ray generating unit 11 according to the embodiment. The X-ray emitted from the X-ray source 10 of the X-ray generating unit 11 passes through the sample, and reaches the detection region of the two-dimensional detector 12. A length of a line segment from an incident position 101 of the X-ray to an outgoing position 102 of the X-ray in the sample 100 is set to length t, and an angle between the normal direction (z direction) to the detection region and a traveling direction of the X-ray is set to angle $\theta$. The maximum position shift due to the difference in the position of the z direction of the sample 100 is $t\sin\theta$. When the $t\sin\theta$ is equal to or less than an extent of the spatial resolution $\Delta$ of the two-dimensional detector 12, the position shift generated in the detected transmission image is reduced. Here, $t\sin\theta$ is equal to or less than the extent of the spatial resolution $\Delta$ means that the $t\sin\theta$ is at least equal to or less than three times the spatial resolution $\Delta$ and is preferred to be equal to or less than twice the spatial resolution $\Delta$. Further, it is more preferable to be equal to or less than the spatial resolution $\Delta$. When the position shift, which occurs in the transmission image of the sample 100, is three times the spatial resolution $\Delta$ of the two-dimensional detector 12, the influence of the position shift can be reduced to an extent that allows blurring by the thickness t of the sample 100 in the image of the stitched transmission image data generated from plurality of transmission images. When the $t\sin\theta$ is twice the spatial resolution $\Delta$, the influence of the position shift can be reduced to an extent that allows a boundary line between portions to become thick by the thickness t of the sample 100 in the image of the stitched transmission image data. Then, when the $t\sin\theta$ is equal to or less than the spatial resolution Δ, the influence of the position shift by the thickness t of the sample 100 can be further reduced in the image of the stitched transmission image data. As a result, it is preferable to reduce the divergence of the X-ray for the tsin θ to be approximately extent of equal to or less than the spatial resolution Δ. If the normal line extending from the center of the detection region of the two-dimensional detector 12 passes through the X-ray source 10, the angle θ of the X-ray that reaches from the X-ray source 10 to the edge of the detection region is largest, and thickness t in the z direction of the sample 100 varies with the shape of the sample 100. Therefore, due to the positioning of the sample 100 or similar, the tsin θ can take various values. If the maximum value of the tsin θ among the varied values is extent of equal to or less than the spatial resolution Δ, the position shift that occurs in the detected transmission image is reduced. This allows generating the stitched transmission image data based on the plurality of transmission images.

The measurement control unit 16 determines an amount of movement of the two-dimensional XY stage 14 based on an amount of overlap where adjacent transmission images partially overlap one another. Furthermore, the measurement control unit 16 controls the two-dimensional XY stage 14 to sequentially move the support base 13 corresponding to the amount of movement, thus allowing the two-dimensional detector 12 to detect the transmission image. Since the position shift of the image caused by the thickness t of the sample 100 does not occur in the detected transmission image, the imaging control unit 17 can generate stitched transmission image data by stitching the transmission images at a plurality of different positions based on the amount of overlap.

Second Embodiment

The X-ray imaging apparatus 1 according to a second embodiment of the present invention is an X-ray imaging apparatus that images a three-dimensional X-ray CT image. The X-ray imaging apparatus 1 according to this embodiment is different from the X-ray imaging apparatus 1 according to the first embodiment in that the support base 13 includes a rotational drive system, and the control unit 15 performs a measurement and an image reconstruction for an imaging of the three-dimensional X-ray CT image. The X-ray imaging apparatus 1 according to this embodiment is otherwise the same as the X-ray imaging apparatus 1 according to the first embodiment.

The rotational drive system of the support base 13 can rotationally move the sample 100 around a rotation axis in a direction (here x direction) along the plane of the detection region of the two-dimensional detector 12 as a rotation axis. The measurement control unit 16 controls the two-dimensional XY stage 14 to move the support base 13 corresponding to aforementioned amount of movement, the rotational drive system of the support base 13 to angularly move the sample 100 sequentially to predetermined number of respective angular positions, and the two-dimensional detector 12 to detect the transmission images in the respective angular positions. The imaging control unit 17 stitches the transmission images at the plurality of different positions in the predetermined number of respective angular positions, thus generating stitched transmission image data. Furthermore, image reconstruction of the stitched transmission image data at the predetermined number of angular positions generates the three-dimensional X-ray CT image.

An X-ray imaging apparatus according to Comparative example 2 will be described before describing an effect of the X-ray imaging apparatus 1 according to this embodiment. Conventionally, the X-ray imaging apparatus for imaging a three-dimensional X-ray CT image includes, for example, a rotational drive system that rotates around a rotation axis (x direction) on which a sample is arranged. The X-ray imaging apparatus rotates the sample with the rotational drive system. The X-ray imaging apparatus takes transmission images at the predetermined number of respective angular positions, performs the image reconstruction with the plurality of taken transmission images, and obtains the three-dimensional CT image. In the case where the transmission image of the whole sample is larger than the detection region of the two-dimensional detector, the obtained three-dimensional CT image is merely an image of a part of the sample. Therefore, in order to obtain a wider range of the three-dimensional CT image, the inventors examined the X-ray imaging apparatus according to Comparative example 2 preceding the present invention.

The X-ray imaging apparatus according to Comparative example 2 is an X-ray imaging apparatus that generates an image of the three-dimensional X-ray CT image, and includes a three-dimensional XYZ stage. The three-dimensional XYZ stage allows the rotational drive system, on which the sample is arranged, to move three-dimensionally (xyz direction). As mentioned above, in the case where the sample size is larger than the detection region of the two-dimensional detector, the obtained three-dimensional CT image is a part of the sample. The three-dimensional XYZ stage sequentially moves the rotational drive system, on which the sample is arranged, and performs an imaging of the three-dimensional X-ray CT image in each of the positions, thus obtaining a three-dimensional CT image for each part of the sample.

Figure 10:
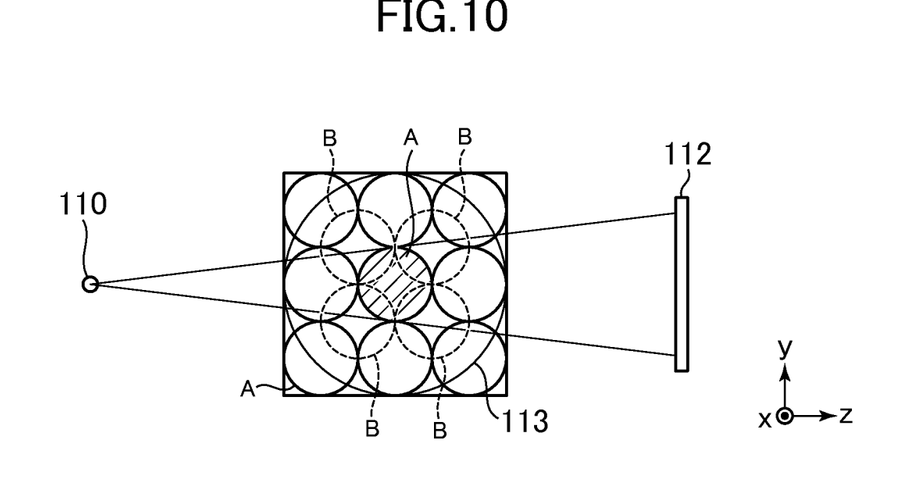
FIG. 10 is a schematic view illustrating an operation of the X-ray imaging apparatus according to Comparative example 2.

FIG. 10 is a schematic view of an operation of the X-ray imaging apparatus according to Comparative example 2. FIG. 10 shows a plane (yz plane) perpendicular to a direction (x direction) of the rotation axis of the rotational drive system. As mentioned above, since the transmission image of the whole sample is larger than the detection region of the two-dimensional detector 112, the three-dimensional CT image in a particular position is a part of the sample. FIG. 10 shows the measurable region A in the present position indicated with the hatched lines. When the sample has the maximum mountable size on a support base 113, the sample size is larger than the measurable region in a particular position as shown in FIG. 10. Thus, a plurality of measurable regions are considered to be arranged to include the whole sample. The length of the sample in the y direction shown in FIG. 10 is about three times (n times) one measurable region, and measurements in 9 (3×3) positions ($n^2$ positions) are required to cover the sample. FIG. 10 shows the 9 measurable regions A indicated with the solid lines. Furthermore, the measurable region in a position has a cross-section with a circle shape. Thus, even if the measurable regions of circle are arranged in the yz plane sequentially, gaps occur in between the measurable regions. In order to obtain a three-dimensional CT image of a part of the gap in the sample, it is further necessary to generate an image of the three-dimensional X-ray CT image in the gap position as the measurable region B. The measurable region B is arranged at the center of square formed by connecting the centers of the measurable regions A arranged in 2×2 (=4 positions) in the yz directions. In the case of FIG. 10, the measurements are required in 4 (2×2) positions ($(n-1)^2$ positions). The measurable regions B in 4 positions are indicated with the dashed lines in FIG. 10. As a result, the imaging of the three-dimensional CT image in 13 positions ($n^2+(n-1)^2$ positions) are necessary in total.

In contrast, in the X-ray imaging apparatus 1 according to this embodiment, when the length of the detection region of the two-dimensional detector is 3 times (n times) the length of the sample (support base 13) in the y direction, it is only necessary to measure the sample 100 in 3 positions (n positions). The measurement positions for the transmission image capture required in order to measure a desired region can be dramatically reduced by the X-ray imaging apparatus according to this embodiment compared with the X-ray imaging apparatus according to Comparative example 2. When the sample is sufficiently larger than the detection region of the two-dimensional detector (when n is large enough), the X-ray imaging apparatus according to Comparative example 2 needs $\{n^2+(n-1)^2\}/n \approx 2(n-1)$ times the measurement positions than the X-ray imaging apparatus according to this embodiment. Also, in regard to the direction (x direction) of the rotation axis of the rotational drive system, the X-ray imaging apparatus according to this embodiment is similar to the X-ray imaging apparatus according to Comparative example 2. When the length of the detection region of the two-dimensional detector is 3 times (n times) the length of the sample in the x direction, the measurements in 3 positions (n positions) are required.

The transmission image taken by the X-ray imaging apparatus according to Comparative example 2 includes transmission information on a part other than the measurable region of the measurement position, thus the obtained three-dimensional CT image includes an artifact (false image). Then, extents of appearance of the artifact in a particular position of the sample are different among the plurality of three-dimensional CT images including the position. Therefore, although the X-ray imaging apparatus according to Comparative example 2 performs the imaging of the three-dimensional X-ray CT image at the plurality of measurement positions such that the measurable regions include the whole sample, it is impossible or extremely difficult to stitch the plurality of three-dimensional X-ray CT images to generate the three-dimensional X-ray CT image of the whole sample for achieving the generation of the three-dimensional X-ray CT image of the whole sample.

In contrast, the X-ray imaging apparatus 1 according to this embodiment stitches the transmission images at the plurality of different positions to generate the stitched transmission image data including the whole sample (large FOV transmission image). Subsequently, the X-ray imaging apparatus 1 performs the imaging of the three-dimensional X-ray CT image by the image reconstruction of the stitched transmission image data in the predetermined number of angular positions. Thus, the problem of the image stitched caused by an artifact generated in the X-ray imaging apparatus according to Comparative example 2 does not occur.

In addition, the X-ray imaging apparatus 1 according to this embodiment is an X-ray imaging apparatus that generates a three-dimensional X-ray CT image. The three-dimensional CT measurement is performed by rotating the sample with the rotational drive system. Also, as shown in the support base 13 of FIG. 1, the maximum mountable sample size (measurable region) on the support base 13 has a circle in the cross section (yz plane) perpendicular to the rotation axis (x direction) of the rotational drive system. That is, the X-ray imaging apparatus 1 according to this embodiment has a measurable region (the maximum measurable sample size) with a columnar shape. The circle has a diameter longer than a length of the detection region of the two-dimensional detector 12 in the y direction and is required to allow the sample 100 with a larger thickness t than the length in the y direction to be measured at the same time. In regard to the thickness t of the sample 100, it is only necessary that aforementioned maximum value of the tθ (formula 1) be about equal to or less than the spatial resolution Δ of the two-dimensional detector 12.

Third Embodiment

The X-ray imaging apparatus 1 according to a third embodiment of the present invention is different from the X-ray imaging apparatus 1 according to the first embodiment in that the X-ray imaging apparatus 1 further includes an optical capture unit 21 and an optical mirror 22 and that the control unit 15 controls a measurement based on an optical image captured by the optical capture unit 21. The X-ray imaging apparatus 1 according to the third embodiment is otherwise similar to the X-ray imaging apparatus 1 according to the first embodiment. Note that, here, the optical image means an image obtained by using the visible region of light. However, it is not limited to visible light; for example, the ultraviolet region of light, the infrared region of light, and other region of light may be employed.

Figure 3:
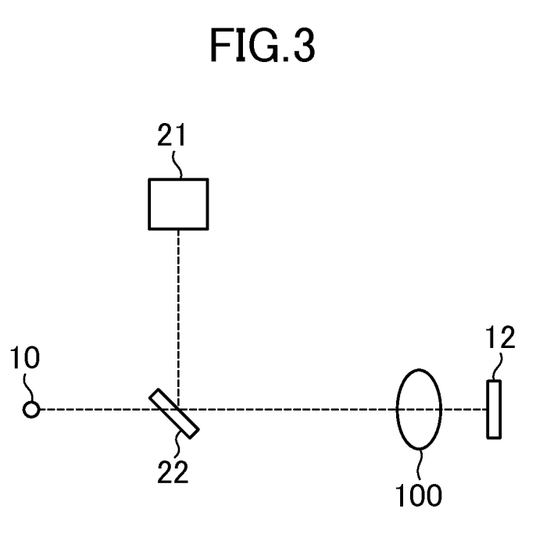
FIG. 3 is a schematic view illustrating a structure of the X-ray imaging apparatus according to a third embodiment of the present invention.

FIG. 3 is a schematic view illustrating a structure of the X-ray imaging apparatus 1 according to this embodiment. For a simple description, a part of the structure is not shown in FIG. 3, but the structure other than the optical capture unit 21 and the optical mirror 22 is shown in FIG. 1. The optical capture unit 21 is, for example, an optical camera and captures an optical image of the sample 100 reflected from the optical mirror 22. The optical mirror 22 is arranged between the X-ray generating unit 11 and the support base 13 to guide the X-ray, which passes through the sample 100 from the X-ray generating unit 11 and reaches the detection region of the two-dimensional detector 12, to the sample side. The optical mirror 22 reflects the light, which travels from the sample 100 along the normal direction (z direction) to the plane of the detection region of the two-dimensional detector 12 (that is, leftward direction of view), into the optical capture unit 21. Here, the optical mirror 22 has an opening portion (aperture: hole with about several millimeters) in a region where the X-ray passes through. The opening portion allows the X-ray, which passes through the sample 100 from the X-ray generating unit 11 and reaches the detection region of the two-dimensional detector 12, to pass without interruption. However, the structure of the optical mirror 22 is not limited to this. For example, the optical mirror 22 may be made of a metal thin film with several tens of micrometers or a multi-layer film. In the cases of the metal thin film and the multi-layer film, these films have a low absorption rate of the X-ray sufficient to the extent that the films do not influence capturing the transmission image and have a high reflection rate with respect to the light from the sample 100 sufficient to the extent in capturing the optical image with the optical capture unit 21. Also, a filter with approximately a thickness of several hundreds of micrometers to absorb the low energy component in the X-ray may be used as an optical mirror.

For example, in the X-ray imaging apparatus 1 according to the first and the second embodiment, the two-dimensional detector 12 can detect only a partial transmission image of the sample detect at a time. Thus, the image of the whole sample cannot be obtained at the step of the measurement start. For example, in the case where the generation of the stitched transmission image data including the whole sample (large FOV transmission image) is desired, a plurality of positions need to be determined for a required plurality of transmission images. The optical image of the sample 100 captured by the optical capture unit 21 is an optical image of the light travelling coaxially with the transmission image detected by the two-dimensional detector 12. Use of the optical image facilitates the control unit 15 to determine and control the measurement condition.

Figure 4:
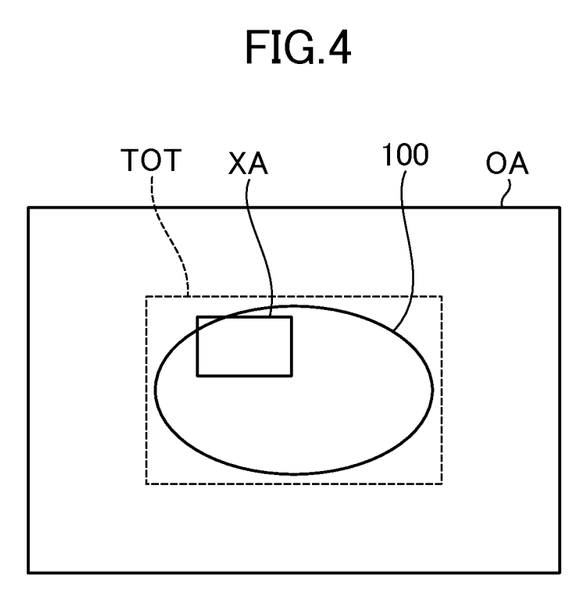
FIG. 4 is a schematic view illustrating an optical image and a transmission image detected by the X-ray imaging apparatus according to the third embodiment of the present invention.

FIG. 4 is a schematic view illustrating an optical image OA and a transmission image XA detected by the X-ray imaging apparatus 1 according to this embodiment. FIG. 4 shows the optical image OA and the transmission image XA. The optical image OA includes the whole image of the sample 100. Overlapping the transmission image XA with the optical image OA allows determining a position relationship between the current sample 100 and the two-dimensional detector 12 with high accuracy. If a region TOT of a stitched transmission image data to be generated is determined based on an image of the sample 100 included in the optical image OA, it is possible to calculate the number of necessary transmission images (respective numbers in x and y directions) and an appropriate overlapping amount of the adjacent transmission images based on the region TOT and apiece of transmission image XA. If the widths of the region TOT and the transmission image XA are respectively set to d1 and d2, the number m of transmission images to be stitched in the x direction (lateral direction) may be m=int(d1÷d2)+1, the overlapping amount Δd of the adjacent transmission images may be Δd=(m×d2−d1)÷(m−1), and the stage moving amount Δx in the x direction may be Δx=d2−Δd. For example, in the case where the width of the region TOT is 1.0 mm and the width of the transmission image XA is 0.4 mm, it gives 1.0÷0.4=2.5; it is only necessary to take three (m=3) pieces of the transmission image in the x direction (lateral direction). In this case, the overlapping amount Δd may be set to (0.4×3−1.0)÷(3−1)=0.1 mm, and the stage moving amount Δx in the x direction may be set to 0.4−0.1=0.3 mm. This process also applies to the y direction (longitudinal direction). Note that the determination method of the measurement condition described here is an example. The measurement condition may increase in the overlapping amount by further increasing the measurement number of piece as necessary. In contrast, the measurement condition may include a further wider range than the region TOT by reducing the overlapping amount.

The measurement control unit 16 of the control unit 15 receives a plurality of necessary pieces of position information (number of measurement, overlapping amount, stage moving amount, and the like) from the outside. The measurement control unit 16 may control the two-dimensional XY stage 14 to perform the measurement of the transmission image based on the information. The measurement control unit 16 may also use the method to calculate the information and perform the measurement control based on the calculated information. Furthermore, the imaging control unit 17 stitches the plurality of taken transmission images based on the information to generate the stitched transmission image. In this process, stitching the transmission images by referring the optical image OA allows obtaining the stitched transmission images with further high accuracy.

Fourth Embodiment

The X-ray imaging apparatus 1 according to a fourth embodiment of the present invention is an X-ray imaging apparatus that generates a three-dimensional X-ray CT image. The X-ray imaging apparatus 1 according to the fourth embodiment is the X-ray imaging apparatus 1 according to the second embodiment where the optical capture unit 21 and the optical mirror 22 according to the third embodiment are applied.

Figure 5:
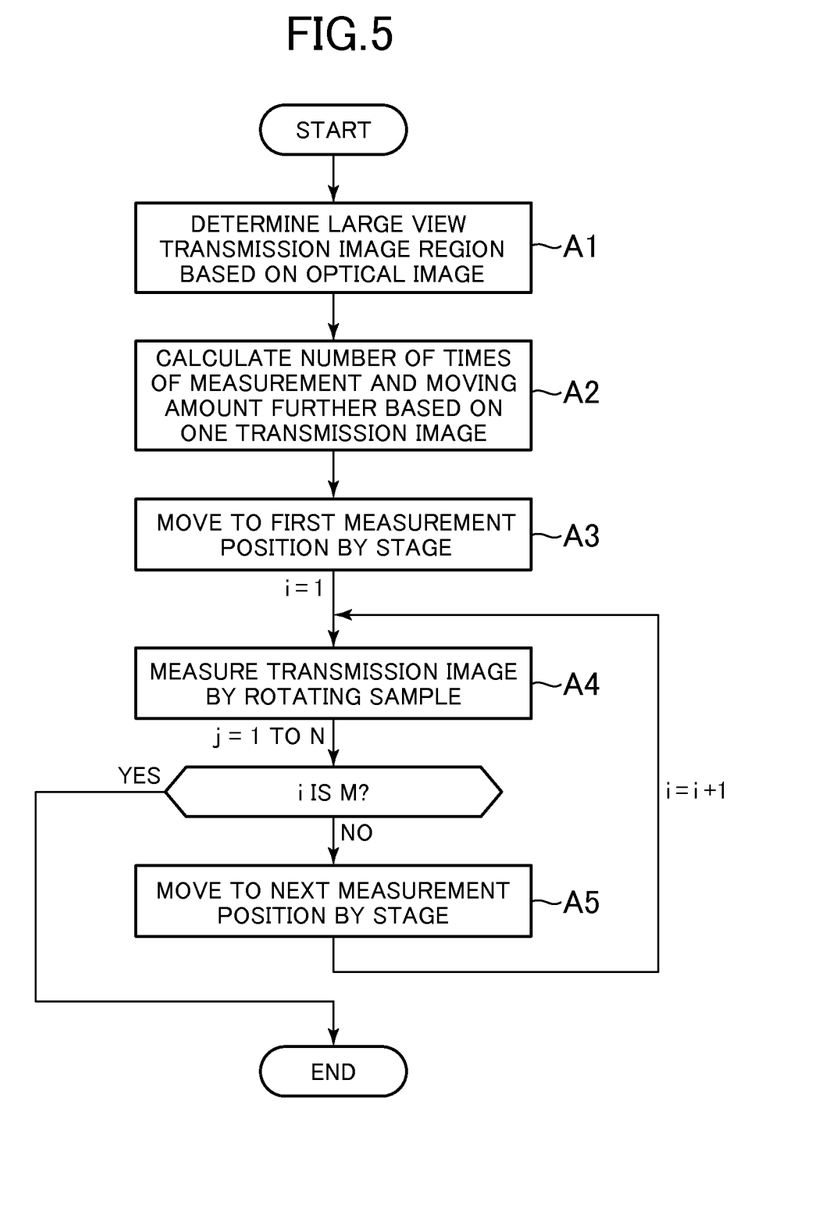
FIG. 5 is a schematic view describing a measurement method of the X-ray imaging apparatus according to a forth embodiment of the present invention.

FIG. 5 is schematic view describing a measurement method of the X-ray imaging apparatus 1 according to this embodiment. As described in the third embodiment, based on the image of the sample 100 included in the optical image OA, the region TOT for stitched transmission image data (large FOV transmission image) to be generated is determined by the external input or the measurement control unit 16 (step A1). Based on the determined region TOT for the stitched transmission image data and one piece of transmission image XA, the measurement control unit 16 calculates the number of times M of the measurements (M measurement positions) of the transmission image necessary for the generation of one piece of stitched transmission image data and the moving amount (stage moving amount) (step A2).

When the necessary measurement condition is decided, the measurement control unit 16 starts to measure. First, the measurement control unit 16 controls the two-dimensional XY stage 14 to move the support base 13, and the sample 100 is set to the first measurement position (step A3). M time measurements, that is, the measurements in M measurement positions are performed as follows. Setting an integer of equal to or more than one and equal to or less than M to i, the i-th measurement of (measurement in i-th measurement position) will be described.

In the i-th measurement, the sample 100 is arranged in the i-th measurement position. In the arrangement of the measurement position, the measurement control unit 16 controls the rotational drive system of the support base 13 to rotationally move the sample 100 sequentially. Setting a predetermined number to N, in each of the N angular positions, the measurement control unit 16 controls the two-dimensional detector 12 to detect a transmission image (step A4), and the measurement control unit 16 stores the data of the transmission image into a memory unit of the control unit 15. Here, if the transmission image is measured for 360 degree image reconstruction, the angular positions are spaced at a constant angle in a range of 0 to 360 degree. If N is to be N=120, the angle between the adjacent angular positions is 360÷120=3 degree, and an integer of equal to or more than one and equal to or less than N is set to j, the j-th angular position is θ=3×(j−1) (j=1, 2, ... 120). In the i-th measurement (measurement in the i-th measurement position), N pieces of transmission image data have been obtained. The measurement control unit 16 controls the two-dimensional XY stage 14 to move the support base 13 and arranges the sample 100 to the next measurement position (i+1-th) (step A5), then the similar measurement is performed. Repeatedly performing M time measurements completes the measurement according to this embodiment. In the last measurement (M-th measurement), the position of the sample 100 is not moved after the transmission image measurement.

In the i-th measurement (i-th measurement position), the transmission image in the j-th angular position is expressed as $Image_{i,j}(x, y)$. The control unit 15 obtains N pieces of transmission image data in each of the M measurement positions. That is, the control unit 15 obtains M×N pieces of transmission image data $Image_{i,j}(x, y)$ in total.

Figure 6A:
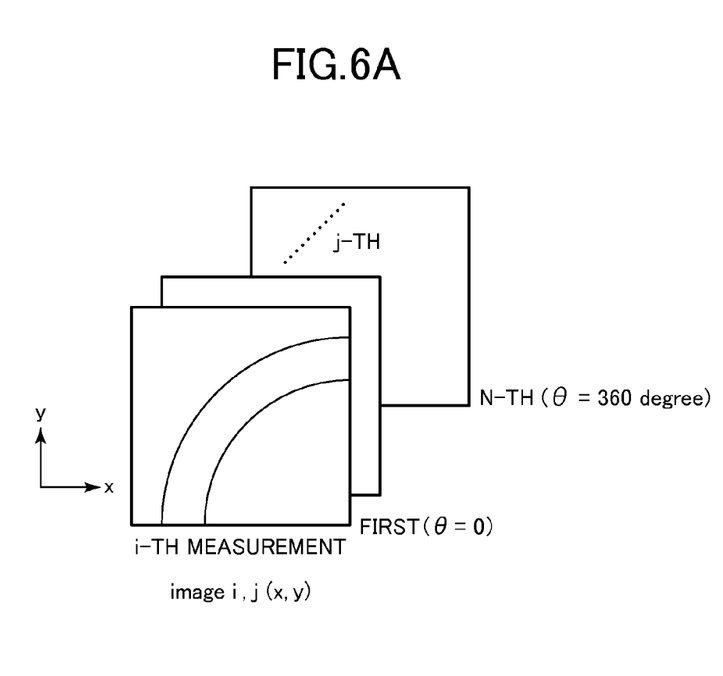
FIGS. 6A and 6B are schematic views describing the transmission image recorded by the measurement method according to the forth embodiment of the present invention.
Figure 6B:
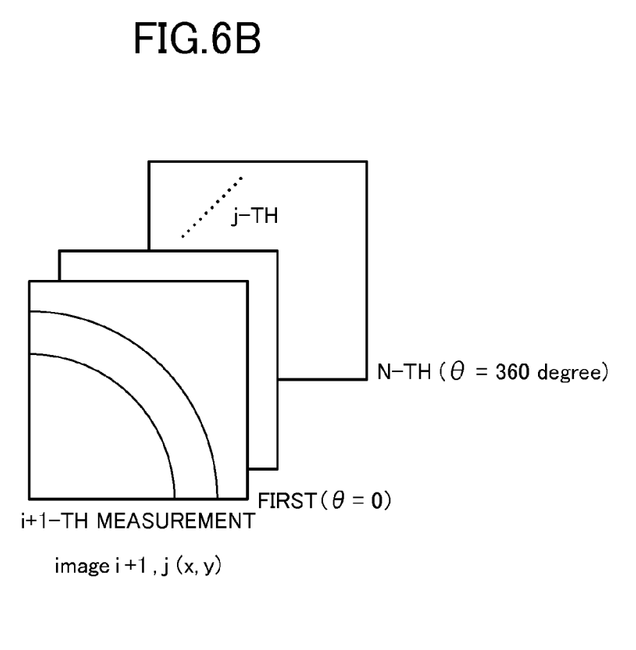

FIGS. 6A and 6B are a schematic view describing the transmission image obtained by the measurement method according to this embodiment. The transmission images in the N angular positions are shown in the i-th measurement and the i+1-th measurement, respectively. That is, the transmission image data shown in FIG. 6A is $Image_{i,j}(x, y)$ and the transmission image data shown in FIG. 6B is $Image_{i+1,j}(x, y)$.

Figure 7:
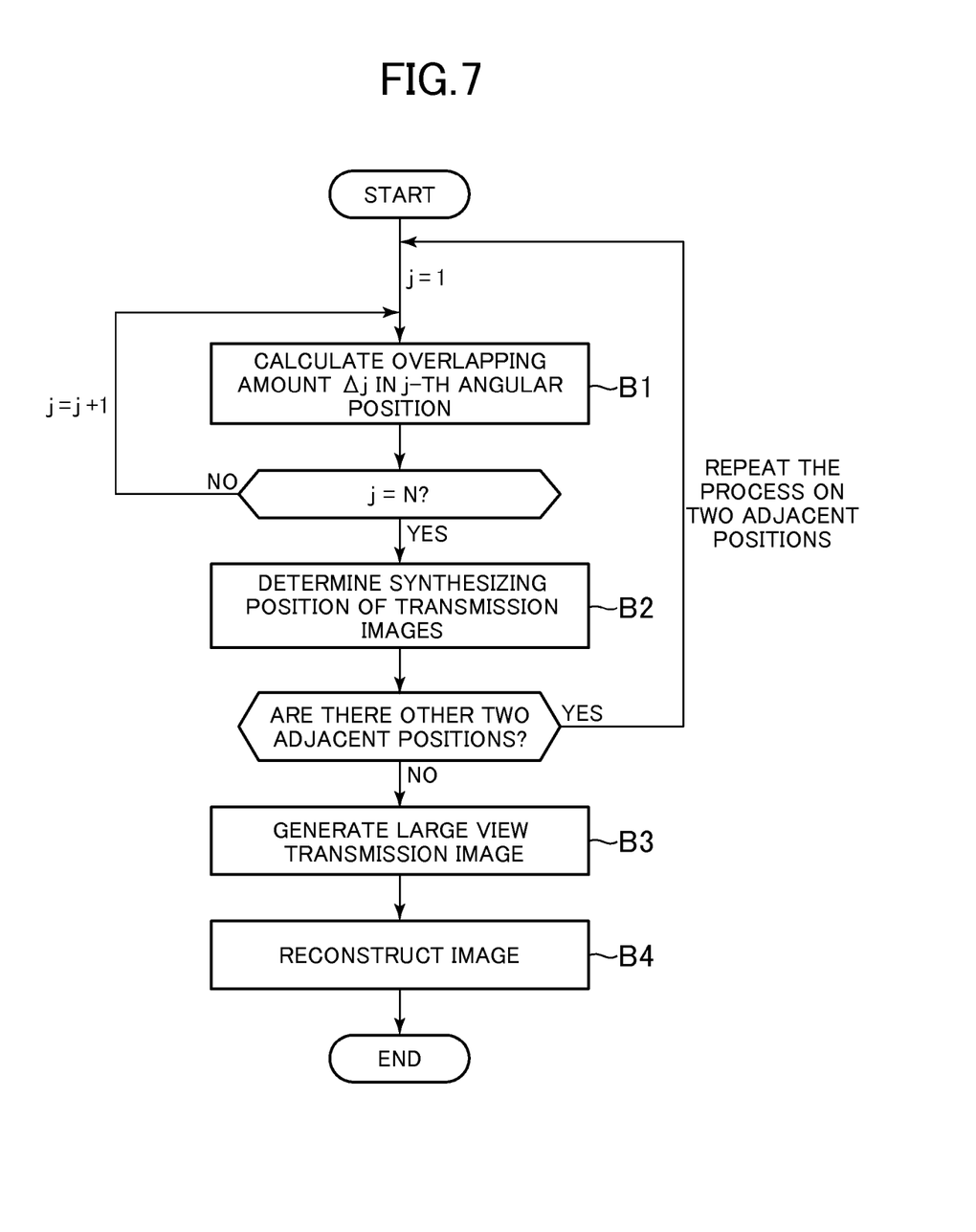
FIG. 7 is a schematic view describing an imaging method of a three-dimensional X-ray CT image of the X-ray imaging apparatus according to the forth embodiment of the present invention.

FIG. 7 is a schematic view describing an imaging method of the three-dimensional X-ray CT image of the X-ray imaging apparatus 1 according to this embodiment. Among M measurement positions in M time measurements, the respective N pieces of transmission image data in the two adjacent measurement positions are stitched. Repeating this process with respect to all the two adjacent measurement positions generates N pieces of stitched transmission image data (large FOV transmission image). By image reconstruction of the N pieces of stitched transmission image data a large-area three-dimensional X-ray CT image is generated.

Here, in the case where the i-th and i+1-th measurement positions are the two adjacent measurement positions, each process of respectively stitching N pieces of transmission image data Image$_{i,j}$(x, y) in the i-th measurement position and N pieces of transmission image data Image$_{i+1,j}$(x, y) in the i+1-th measurement position shown in FIGS. 6A and 6B will be described.

Figure 8:
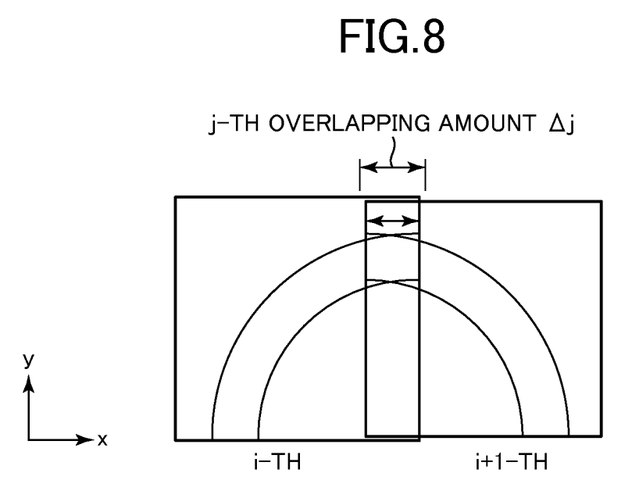
FIG. 8 is a schematic view describing the transmission image recorded by the measurement method according to the forth embodiment of the present invention.

FIG. 8 is a schematic view describing a transmission image obtained by the measurement method according to the embodiment. The transmission images obtained at the respective j-th angular positions in the i-th and i+1-th measurements are shown in FIG. 8, respectively.

Respective signal intensity distributions of two pieces of transmission image data Image$_{i,j}$(x, y) and Image$_{i+1,j}$(x, y) in j-th angular position (j is in a range of 1 to N) are examined to calculate the overlapping part (overlapping amount) of the two pieces of transmission image data (step B1). The overlapping amount $\Delta_j$ of the images in the j-th angular position is calculated (method of least squares) such that the sum of squares of respective differences in signal intensities of the i-th coordinate (x, y) and the i+1-th coordinate (x', y') is minimized. Performing this process on all the N angular positions determines stitching positions of the transmission images in respective angular positions (step B2). Here, the rotational drive system of the support base 13 has an angle accuracy that is higher than an angle accuracy of the two-dimensional XY stage 14. Thus, the overlapping amounts in the respective angular positions are assumed to be equal ($\Delta_1 = \ldots = \Delta_j = \Delta_{j+1} \ldots = \Delta_N$). The sum of squares of respective differences in signal intensities in the i-th coordinate (x, y) and the i+1-th coordinate (x', y') is calculated for the N pieces of transmission image data. The overlapping amounts $\Delta$ for the minimum sums are also calculated. Performing this process on all the two adjacent measurement positions generates N pieces of stitched transmission image data (large FOV transmission image) (step B3). In addition, processing a well-known image reconstruction with the N pieces of stitched transmission image data (step B4) completes imaging of the desired three-dimensional X-ray CT image.

The feature of the three-dimensional CT measurement in the three-dimensional X-ray CT apparatus according to this embodiment is as follows. The two-dimensional XY stage 14 sequentially moves the support base 13. The sample 100 is set to be at the i-th position arrangement and is fixed to the i-th position arrangement. In the position arrangement, the rotational drive system of the support base 13 rotates the sample 100 for detecting N pieces of transmission images. Repeating this process for the M position arrangements allows measuring the three-dimensional CT. This measurement method can shorten the measurement time and achieve more highly accurate measurement at the same time compared with the case of repeating the process for the N angular positions. In the repeated process, the sample 100 is fixed to the angular positions of the rotational drive system, the two-dimensional XY stage 14 moves the sample 100 to the plurality of positions, and M pieces of transmission images are detected. This is because the rotational drive system of the support base 13 has a higher angular accuracy than a position accuracy of the two-dimensional XY stage 14 and the rotational drive system drives faster than driving for moving the two-dimensional XY stage 14.

In this embodiment, this three-dimensional CT measurement method is employed. The imaging method of the three-dimensional X-ray CT image according to this embodiment applies the method of least squares to all the N pieces of transmission images to determine the respective stitching positions of the N pieces of transmission images and to calculate the overlapping amount $\Delta$ in two adjacent measurement positions. Use of all the N pieces of transmission images obtained in the two adjacent measurement positions, and stitching the transmission images in the two adjacent measurement positions allow easily determining the stitching position with high accuracy. Moreover, the optical image taken by the optical capture unit 21 may be stored in the memory unit, and when calculating the overlapping amount of the transmission images in the two adjacent measurement positions, the fine adjustment of the overlapping amount may be performed using this optical image.

Furthermore, even if the order of movement to the N angular positions and movement (parallel movement) to the M measurement positions is switched, the present invention is applicable. That is, the following process may be repeated with respect to the N angular positions. The sample 100 is fixed to the j-th angular position. In this angular position, the two-dimensional XY stage 14 moves the sample 100 to each of the M measurement positions, and M pieces of transmission images are detected. With the M×N pieces of transmission image data thus obtained, use of the imaging method of the three-dimensional X-ray CT image shown in FIG. 7 generates N pieces of stitched transmission image data (large FOV transmission image). By the image reconstruction of the N pieces of stitched transmission image data, a large-area three-dimensional X-ray CT image is generated.

In the above, the X-ray imaging apparatus and the X-ray imaging method according to the present invention are described. Here, the imaging of a piece of stitched transmission image (large FOV transmission image) and the imaging of three-dimensional X-ray CT image reconstructed from the plurality of pieces of stitched transmission image are described as an example. This, however, should not be construed in a limiting sense. For example, this is widely applied to a micro X-ray diffractometer, a scanning fluorescence X-ray spectrometer, and similar apparatus.

Further, the X-ray generating unit 11 according to the embodiments of the present invention irradiates directly the sample 100 with the X-ray emitted from the X-ray source 10. This, however, should not be construed in a limiting sense. For example, the X-ray generating unit 11 may include a multilayer film mirror where a reflective curved surface is a part of parabola, thus the divergence of the X-ray is reduced (parallel X-ray), and a sample may be irradiated with a substantially parallel X-ray.

While there have been described what are at present considered to be certain embodiments of the invention, it will be understood that various modifications may be made thereto, and it is intended that the appended claims cover all such modifications as fall within the true spirit and scope of the invention.

What is claimed is:
1. An X-ray imaging apparatus comprising:
an X-ray generating unit configured to irradiate a sample with substantially parallel X-rays;
a two-dimensional detector arranged at an opposite side of the X-ray generating unit with respect to the sample, the two-dimensional detector including a detection region to detect a transmission image of the sample, the two dimensional detector being fixed during detection of the transmission image of the sample;
a support base where the sample is arranged;
a stage where the support base is mounted, the stage being configured to translationally move the support base in a stage plane along a detection plane of the detection region of the two-dimensional detector; and a control unit configured to generate stitched transmission image data based on a plurality of transmission images of the sample at a plurality of positions of translational motion in the stage plane detected by the two-dimensional detector, wherein the control unit is configured to stitch the transmission images of the sample at the plurality of positions of translational motion in the stage plane to generate the stitched transmission image data.

2. An X-ray imaging apparatus according to claim 1, wherein the support base includes a rotational drive system with a rotation axis in a direction along the detection plane of the detection region, the rotational drive system being configured to rotationally move the sample to a predetermined number of respective angular positions, and the control unit is configured to:
  stitch the plurality of transmission images of the sample at the plurality of positions of translational motion in the stage plane in each of the predetermined number of angular positions to generate the stitched transmission image data in the predetermined number of angular positions; and
  perform image reconstruction with the predetermined number of pieces of stitched transmission image data generated so as to obtain a three-dimensional X-ray CT image.

3. An X-ray imaging apparatus according to claim 2, wherein the stage is configured to sequentially move the support base to arrange the sample in a position among the plurality of positions of translational motion in the stage plane, in the arrangement of the position, the rotational drive system rotationally moves the sample to sequentially arrange the sample in an angular position among the predetermined number of angular positions, in the arrangement, the two-dimensional detector detects a transmission image of the sample, and in the predetermined number of respective angular positions, a plurality of transmission images are detected in the plurality of mutually different positions in the sample.

4. An X-ray imaging apparatus according to claim 1, further comprising:
  an optical capture unit configured to capture an optical image of the sample; and
  an optical mirror arranged between the X-ray generating unit and the support base, the optical mirror being configured to allow an X-ray to pass from the X-ray generating unit to the sample, the optical mirror being configured to reflect light travelling from the sample along a normal direction to the plane of the detection region to enter the light into the optical capture unit.

5. An X-ray imaging apparatus according to claim 4, wherein
  the optical mirror includes an opening portion through which an X-ray passes, the X-ray reaching the detection region of the two-dimensional detector from the X-ray generating unit.

6. An X-ray imaging apparatus according to claim 4, wherein
  the optical mirror is a metal thin film mirror.

7. An X-ray imaging apparatus according to claim 1, wherein
  assuming that a distance from the X-ray generating unit to the sample is L and a distance from the sample to the two-dimensional detector is d, a value of d/L is equal to or less than 0.1.

8. An X-ray imaging apparatus according to claim 1, wherein
  regarding an X-ray that enters the sample and passes through the sample to reach the detection region of the two-dimensional detector, assuming that a distance from an incident position to an outgoing position in the sample is t and an angle between a normal direction to the detection region and a traveling direction of the X-ray is $\theta$, t being sufficiently larger than a spatial resolution of the two-dimensional detector, and any to $t\sin\theta$ being equal to or less than the spatial resolution of the two-dimensional detector.

9. An X-ray imaging method comprising:
irradiating a sample with substantially parallel X-rays;
translationally moving the sample in a stage plane along a detection plane of a detection region of a two-dimensional detector;
detecting a plurality of transmission images of the sample at a plurality of positions of translational motion in the stage plane using the two-dimensional detector, the two dimensional detector being fixed during detection of the transmission image of the sample, and
stitching the plurality of transmission images of the sample at the plurality of positions of translational motion in the stage plane to generate the stitched transmission image data.

* * * * *